United States Patent [19]
Miyawaki

[11] Patent Number: 5,551,440
[45] Date of Patent: Sep. 3, 1996

[54] ELECTRONIC BLOOD PRESSURE METER

[75] Inventor: Yoshinori Miyawaki, Yawata, Japan

[73] Assignee: OMRON Corporation, Kyoto, Japan

[21] Appl. No.: 395,640

[22] Filed: Feb. 28, 1995

Related U.S. Application Data

[63] Continuation of Ser. No. 153,281, Nov. 17, 1993, abandoned, which is a continuation of Ser. No. 839,284, Feb. 25, 1992, abandoned, which is a continuation of Ser. No. 689,099, Apr. 22, 1991, abandoned, which is a continuation of Ser. No. 465,650, Jan. 22, 1990, abandoned, which is a continuation of Ser. No. 323,026, Mar. 15, 1989, abandoned.

[30] Foreign Application Priority Data

Mar. 15, 1988 [JP] Japan .................................. 63-60750
Mar. 17, 1988 [JP] Japan .................................. 63-64334

[51] Int. Cl.$^6$ ............................................. A61B 5/0225
[52] U.S. Cl. ......................... 128/681; 128/682; 128/677; 128/672
[58] Field of Search ........................... 128/672, 677–686

[56] References Cited

U.S. PATENT DOCUMENTS

| | | |
|---|---|---|
| 3,903,872 | 9/1975 | Link . |
| 4,140,110 | 2/1979 | Jansen et al. .......................... 128/681 |
| 4,313,445 | 2/1982 | Georgi ................................. 128/682 X |
| 4,418,700 | 12/1983 | Warner ................................. 128/672 |
| 4,546,775 | 10/1985 | Medero ................................ 128/681 |
| 4,651,747 | 3/1987 | Link ................................... 128/672 |

FOREIGN PATENT DOCUMENTS

| | | |
|---|---|---|
| 2412298 | 5/1978 | France . |
| WO-A-8600211 | 6/1985 | WIPO . |

OTHER PUBLICATIONS

L. A. Geddes et al., "Characterization of the Oscillometric Method for Measuring Indirect Blood Pressure", *Annals of Biomedical Engineering*, vol. 10, pp. 271–280 (1982).

*Primary Examiner*—David M. Shay
*Attorney, Agent, or Firm*—Fish & Richardson P.C.

[57] ABSTRACT

An electronic blood pressure meter which determines a systolic blood pressure value and a diastolic blood pressure value by detecting a sharpest positive peak and a sharpest negative peak of a pulse wave, respectively, which may be extracted from a cuff pressure. The sharpest peaks may be detected by finding the points of intersection of the pulse wave level with a certain threshold level and finding the shortest time interval between adjacent points of intersection interposing a peak therebetween. Since the principle of measurement is exact and can be implemented as a relatively simple algorithm, accurate measurement is possible substantially without any exception.

7 Claims, 8 Drawing Sheets

ELECTRONIC BLOOD PRESSURE METER

This application is a continuation of U.S. application Ser. No. 08/153,281, filed Nov. 17, 1993, now abandoned, which is a continuation of Ser. No. 07/839,284, filed Feb. 25, 1992, now abandoned, which is a continuation of U.S. application Ser. No. 07/689,099, filed Apr. 22, 1991, now abandoned, which is a continuation of U.S. application Ser. No. 07/465,650, filed Jan. 22, 1990, now abandoned, which is a continuation of U.S. application Ser. No. 323,026, filed Mar. 15, 1989, now abandoned.

TECHNICAL FIELD

The present invention relates to an electronic blood pressure meter based on the oscillation method, and in particularly to an electronic blood pressure meter which determines a diastolic blood pressure value and a systolic blood pressure value as the cuff pressure values at the time of occurrence of a sharpest negative peak and a sharpest positive peak of the pulse wave which are produced at cardiac expansion and contraction periods, respectively.

BACKGROUND OF THE INVENTION

Conventionally, according to electronic blood pressure meters based on the oscillation method, diastolic and systolic blood pressure values are measured as described in the following. First of all, a cuff is applied to the upper arm of the subject and the air in the cuff is pressurized by a pump or the like to apply pressure to his upper arm and temporarily block the blood flow in the artery therein.

As the air in the cuff is gradually released at a constant rate, a variable component is found in the air pressure in the cuff (which is referred to as "cuff pressure" hereinafter) as shown in FIG. 8(c). This variable component which is called as pulse wave represents the change in the internal volume of the artery, and is transmitted from the artery to the cuff through the soft tissues of the upper arm as a variation in pressure.

A series of amplitude values Ap are separated and computed from the pulse wave through a filtering process (refer to FIGS. 8(b) and 8(c)). A maximum amplitude value $Ap_{max}$ is extracted from the amplitude values Ap, and an amplitude value $Ap_{0.7}$ corresponding to a 70% level of the maximum amplitude value $Ap_{max}$ occurring before the occurrence of $Ap_{max}$ is also extracted. The cuff pressure Pc at the occurrence of $Ap_{0.7}$ is determined as a systolic blood pressure value SYS.

Meanwhile, a critical point $A_{PD}$ is detected as an amplitude value corresponding to the point of change from a rapid decrease to a gradual decrease of the pulse wave amplitude Ap after the occurrence of the maximum pulse wave amplitude value $Ap_{max}$. The cuff pressure Pc corresponding to the occurrence of $A_{PD}$ at $t_D$ is determined as a diastolic blood pressure value DIA.

Since the above described process of blood pressure determination is based on a statistical principle, it is not entirely free from measurement errors when the subject is an aged person or a person suffering from high blood pressure. Further, the critical point $A_{PD}$ is not very clear depending on the subject, and it may often happen that the determination of a diastolic blood pressure value DIA is not possible.

BRIEF SUMMARY OF THE INVENTION

In view of such problems of the prior art, a primary object of the present invention is to provide an electronic blood pressure meter which is accurate in operation and easy to be implemented.

A second object of the present invention is to provide an electronic blood pressure meter which can measure blood pressure values in a short period of time.

A third object of the present invention is to provide an electronic blood pressure meter which is reliable in the sense that the chance of measurement failure is extremely small.

These and other objects of the present invention can be accomplished by providing an electronic blood pressure meter, comprising: a cuff; pressurization means for pressurizing fluid in said cuff; depressurization means for rapidly or gradually depressurizing said fluid in said cuff; pressure detecting means for detecting said pressure of said fluid in said cuff; pulse wave detecting means for detecting a pulse wave at a part of a subject to which said cuff is applied; and blood pressure value determining means for determining a blood pressure value according to said fluid pressure detected by said pressure detecting means and said pulse wave detected by said pulse wave detecting means; further comprising: peak extracting means for extracting a sharpest peak from said pulse wave detected by said pulse wave detecting means, said blood pressure value determining means determining said fluid pressure of said cuff corresponding to said sharpest peak detected by said peak extracting means as a blood pressure value.

The sharpest peaks may be detected by finding the points of intersection of the pulse wave level with a certain threshold level and finding the shortest time interval between adjacent points of intersection interposing a peak therebetween. If a negative peak is interposed a diastolic blood pressure value can be detected, and if a positive peak is interposed a systolic blood pressure value can be detected.

Alternatively, a diastolic blood pressure value may be detected by finding the shortest time interval between a point of intersection of said pulse wave level with a threshold level as said pulse wave level is decreasing and a next point of intersection of said pulse wave level with said threshold level as said pulse wave level is increasing. Conversely, a systolic blood pressure value may be detected by finding the shortest time interval between a point of intersection of said pulse wave level with a threshold level as said pulse wave level is increasing and a next point of intersection of said pulse wave level with said threshold level as said pulse wave level is decreasing.

Now the functional aspects of the present invention are described in the following with reference to FIG. 7.

The cuff pressure Pc is transmitted to the outer wall of the blood vessel via the soft tissues to which the cuff is applied. This pressure acts in the direction to flatten the blood vessel, but the internal pressure Pa of the blood vessel acts in the direction to expand the blood vessel. The internal volume V of the blood vessel is determined as a balance between the cuff pressure Pc and the internal pressure Pa of the blood vessel. The relationship between the transmural pressure Pt (pressure difference between pressures acting in and out of the blood vessel; =Pa −Pc) and the internal volume V of the blood vessel is shown in FIG. 7.

The internal pressure of the blood vessel Pa is always fluctuating and it accordingly changes the internal volume of the blood vessel V. This change in the internal volume of the blood vessel V is transmitted to the cuff via the soft tissues. Since the volume change of the cuff is so small as compared with the total volume of the cuff that it can be assumed that the change in the internal volume of the blood vessel V is proportional to the change in the cuff pressure. In other words, the pulse wave generated in the cuff substantially corresponds to the internal volume of the blood vessel V.

The graph of FIG. 7 represents the transmural pressure Pt along the horizontal axis and the internal volume of the blood pressure V along the vertical axis. The transmural pressure Pt can be given by the following equation of the variational component of blood pressure ΔP, average blood pressure M and cuff pressure Pc:

$$Pt = \Delta P + M - PC \quad (1)$$

M and Pc contribute to the change in the absolute position of the Pt–V curve. ΔP is converted into a volume pulse wave by the Pt–V curve, and this volume change is detected as a pulse wave as mentioned earlier.

As can be seen from FIG. 7 showing the blood vessel properties, the change in the internal pressure of the blood vessel V is maximized for a given change in Pt when Pt is zero. In other words, the blood vessel is most compliant when the transmural pressure Pt is zero.

Therefore, as shown by the pulse wave of the internal pressure of the blood vessel $W_4$, the negative peak of the internal volume of the blood vessel converted by the Pt–V curve or the negative peak of the pulse wave $P_4$ which is proportional thereto becomes sharpest at the point of diastolic blood pressure (the leftmost point of the pulse wave $W_4$ in FIG. 7) where Pt=0.

On the other hand, at the pulse wave $W_1$ where the blood vessel is substantially completely flattened, the change in the internal volume of the blood vessel is small for a given change in the internal pressure of the blood vessel, and the negative peak of the pulse wave $P_6$ waveform becomes bluntest.

Thus, the cuff pressure at which the negative peak of the pulse wave waveform becomes sharpest can be determined as a diastolic blood pressure value.

Likewise, as shown by the pulse wave of the internal pressure of the blood vessel $W_2$, the positive peak of the internal volume of the blood vessel converted by the Pt–V curve or the positive peak of the pulse wave $P_2$ which corresponds thereto becomes sharpest at the point of systolic blood pressure (the rightmost point of the pulse wave $W_2$ in FIG. 7) where Pt=0.

Thus, the cuff pressure at which the positive peak of the pulse wave waveform becomes sharpest can be determined as a systolic blood pressure value.

BRIEF DESCRIPTION OF THE DRAWINGS

Now the present invention is described in the following in terms of specific embodiments with reference to the appended drawings, in which.

DESCRIPTION OF THE PREFERRED EMBODIMENTS

Figure 1:
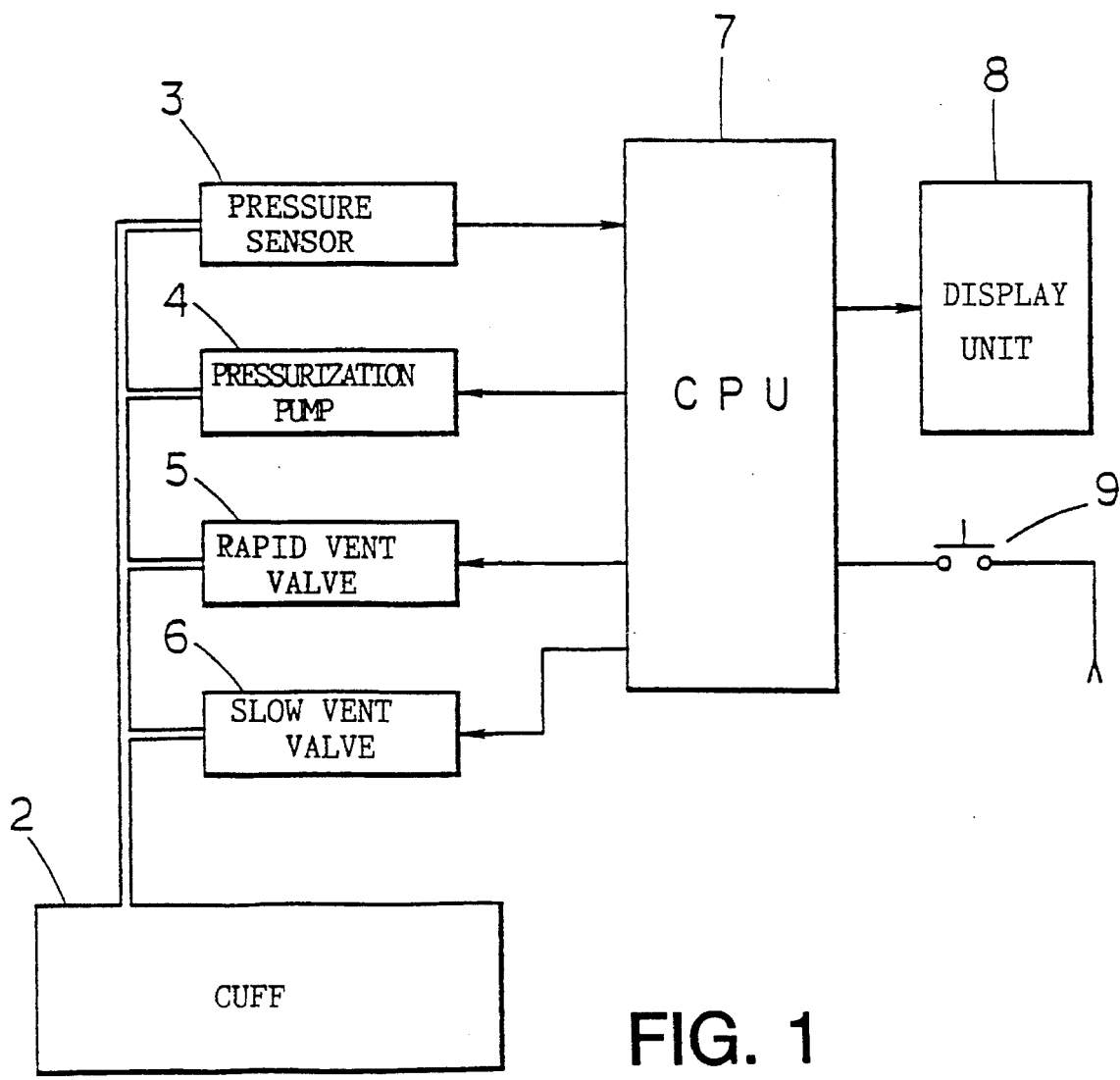
FIG. 1 is a block diagram illustrating the structure of an electronic blood pressure meter based upon an embodiment of the present invention.
Figure 2:
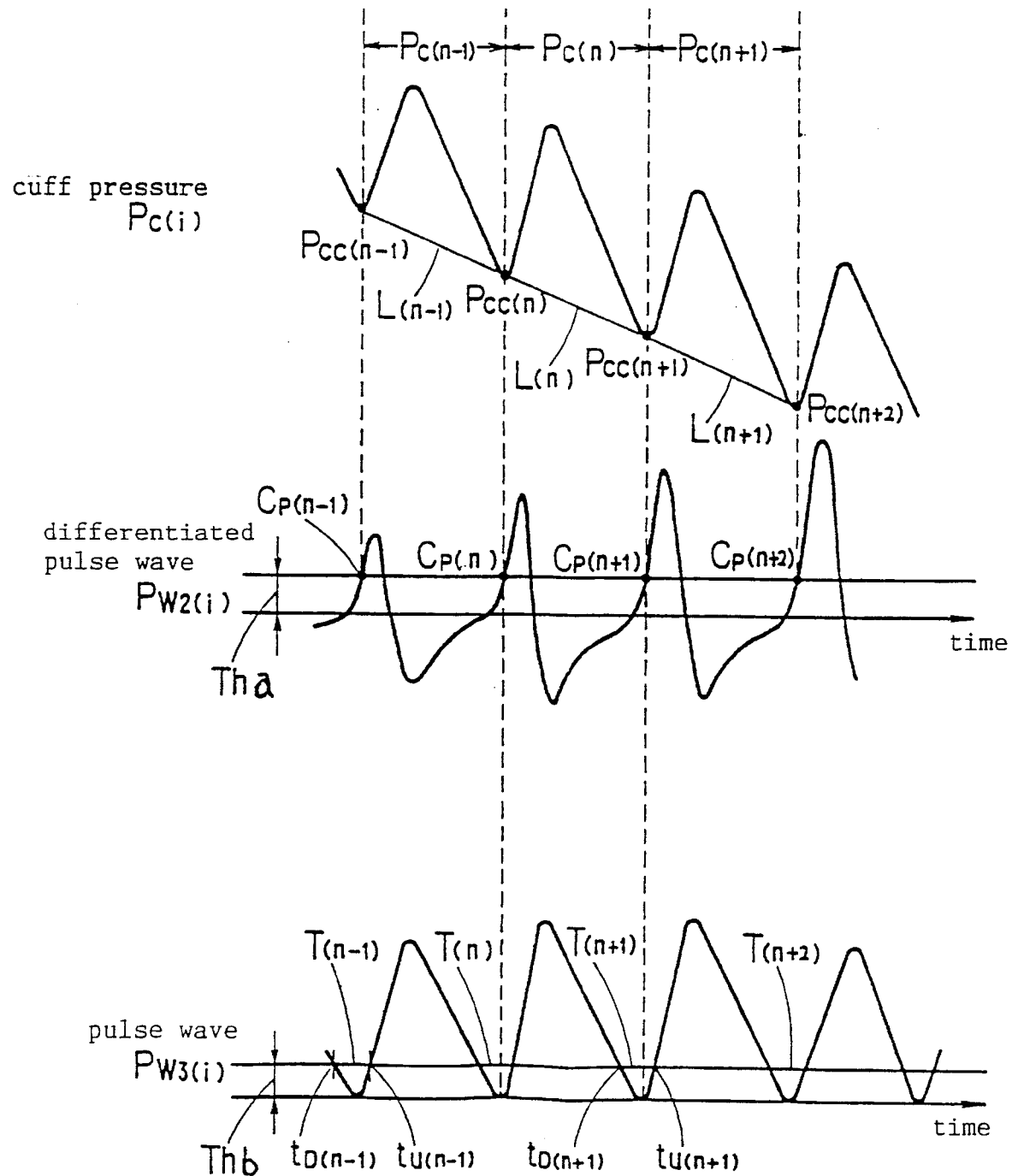
FIG. 2 is a waveform diagram for illustrating the process of processing pulse wave data in an electronic blood pressure meter.

Now an embodiment of the present invention is described in the following with reference to FIGS. 1 through 3.

Figure 3:
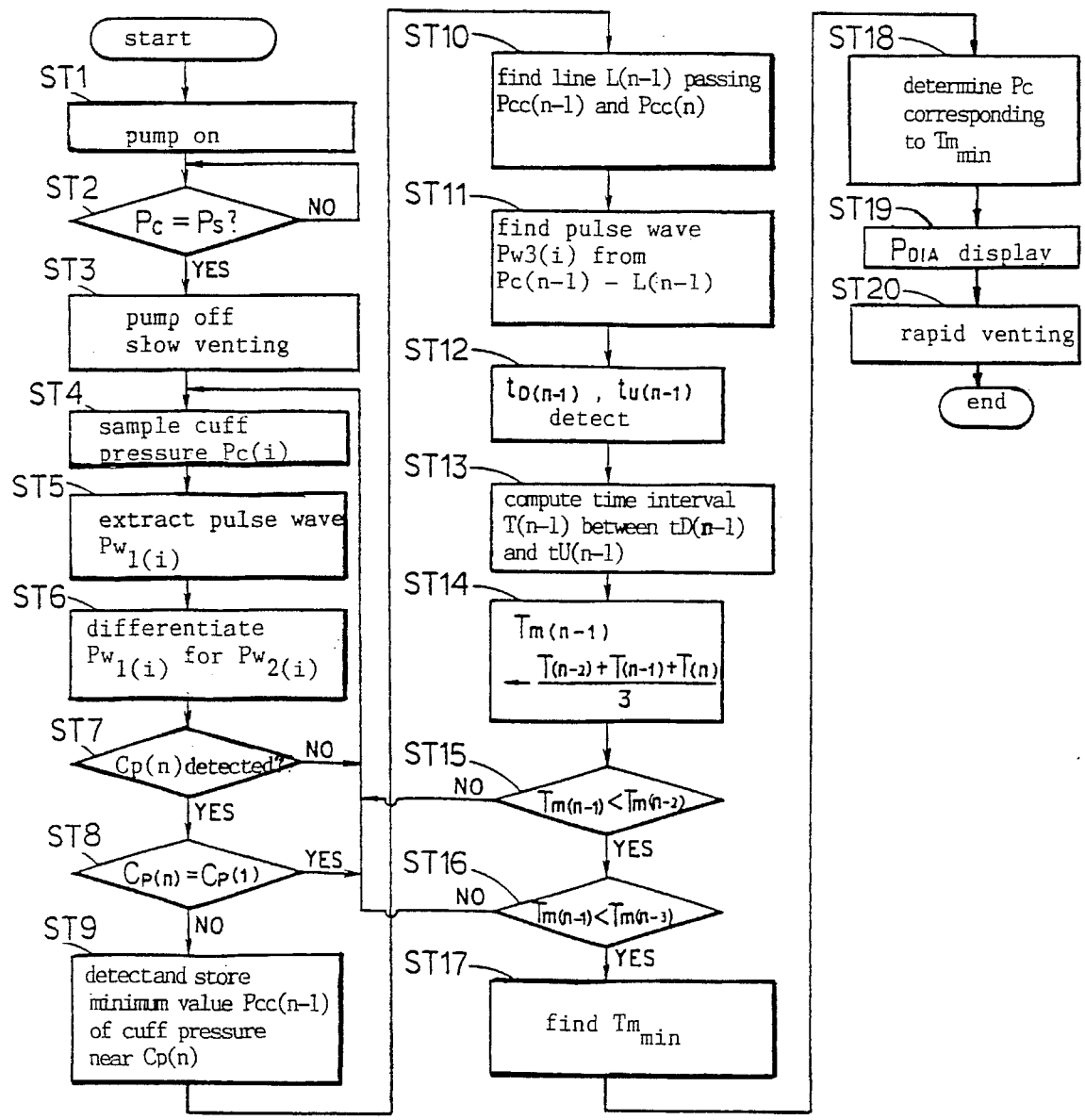
FIG. 3 is a flow diagram illustrating the operation of the electronic blood pressure meter.

In this embodiment, the present invention is applied to an arm band type electronic blood pressure meter, and FIG. 3 is a block diagram illustrating the structure of the electronic blood pressure meter of this embodiment.

Numeral 2 denotes a cuff of a known type, which is connected to a pressure sensor (pressure detecting means) 3, a pressurization pump (pressurization means) 4, a rapid vent valve (depressurization means) 5, and a slow vent valve (depressurization means) 6. The output signal of the pressure sensor 3 is fed to a CPU 7. The pressurization pump 4, the rapid vent valve 5 and the slow vent valve 6 are controlled by the CPU 7.

The CPU 7 is provided with various functions such as detecting a pulse wave from the output signal of the pressure sensor 3 and detecting the sharpest peaks from the detected pulse wave. The CPU 7 is connected to a display unit 8 of an LCD type and a start switch 9.

Now the operation of this electronic blood pressure meter is described in the following.

First of all, the cuff 2 is applied to the upper arm of the subject. Then, the start switch 9 is turned on to start the operation of the pressurization pump 4 and start the process of pressurizing the cuff 2 (step 1 or ST1). In ST2, it is determined whether the cuff pressure Pc agrees with a target pressure value Ps. If the determination result is negative, the program flow continues a process of waiting until the cuff 2 is fully pressurized. However, if the determination result is affirmative, the program flow branches off to ST3.

In ST3, the CPU 7 stops the operation of the pressurization pump 3 and, at the same time, opens the slow vent valve 6 to start the process of gradual depressurization.

In ST4, the cuff pressure values $Pc_{(i)}$ are sampled. The sampling period of this sampling process is normally 10 to 50 milliseconds, and "i" denotes the serial number of the sampling points. In ST5, a digital sampling process is performed on the sampled values $Pc_{(i)}$ to extract pulse wave values $Pw_{1(i)}$. In ST6, differentiated pulse wave values $Pw_{2(i)}$ are obtained by differentiating the pulse wave values $Pw_{1(i)}$ (refer to FIG. 1).

In ST7, it is determined whether the point $Cp_{(n)}$ where the differentiated pulse wave level $Pw_{2(i)}$ exceeds a certain threshold level Tha has been detected. The point $Cp_{(n)}$ is the point which divides the pulse wave, and if the result of this determination process is negative, the program flow returns to ST4 to repeat the sampling of the cuff pressure values $Pc_{(i)}$. If the result of the determination process of ST7 is affirmative, the program flow advances to the determination process of ST8. In ST8, it is determined whether $Cp_{(n)}$ is equal to $Cp_{(1)}$. If so, the program flow returns to ST4. This step is provided for the purpose of determining whether there are two or more $Cp_{(n)}$ data because the process following ST9 cannot be executed if that is not the case.

If the determination result of ST8 is affirmative, the program flow branches off to ST9, and a minimum value of the cuff pressure $Cp_{(i)}$ near the time point of $Cp_{(n)}$ is detected as $Pcc_{(n)}$. Then, in ST10, a line $L_{(n-1)}$ passing through both previously detected $Pcc_{(n-1)}$ and current $Pcc_{(n)}$ is computed. Finally, a pulse wave $Pw_{3(i)}$ is computed by subtracting the line $L_{(n-1)}$ from cuff pressure waveform $Pc_{(n-1)}$ between $Pcc_{(n-1)}$ and $Pcc_{(n)}$ (ST11).

The reason for obtaining the pulse wave $Pw_{3(i)}$ by subtracting $L_{(n-1)}$ from $Pc_{(n-1)}$ is that the pulse wave $Pw_{1(i)}$ detected by digital filtering has a distorted waveform which is not suitable for detecting the sharpest negative peak.

In ST12 are detected points $t_{D(n-1)}$ and $t_{U(n-1)}$ at which $Pw_{3(i)}$ intersects the threshold level Thb as it falls and rises, respectively. The threshold level Thb is typically set between 0.1 and 0.5 mmHg, but may also be a relative value such as so many percent of each peak of the pulse wave $Pw_{3(i)}$ instead of such an absolute value.

In next ST13, a time interval $T_{(n-1)}$ between $t_{D(n-1)}$ and $t_{U(n-1)}$ is computed and stored. This time interval $T_{(n-1)}$ is a variable for evaluating the sharpness of the negative peaks, and the smaller this value is the sharper the peak is.

In ST14, $T_{(n-1)}$ is smoothed into $Tm_{(n-1)}$ according to equation (2) given below:

$$Tm_{(n-1)}=(T_{(n-2)}+T_{(n-1)}+T_{(n)})/3 \qquad (2)$$

This is performed for the purpose of reducing the effects of such artifact interferences as respiratory irregular pulses and body motions.

In ST15 and ST16, inequalities $Tm_{(n-1)}<Tm_{(n-2)}$ and $Tm_{(n-1)}<Tm_{(n-3)}$ are evaluated; the program flow advances to ST17 only when both the inequalities hold but otherwise returns to ST4.

In ST17, a minimum value is selected from $Tm_{(1)}$ through $Tm_{(n-1)}$ which have been computed so far and is defined as $Tm_{MIN}$. In ST18, the cuff pressure Pc corresponding to $Tm_{MIN}$ is set as a diastolic blood pressure value $P_{DIA}$. This diastolic blood pressure value $P_{DIA}$ as well as the systolic blood pressure value $P_{SYS}$ is displayed on the display unit 8 (ST19) and the rapid vent valve 5 is opened to release the upper arm of the subject from pressurization (ST20).

Figure 4:
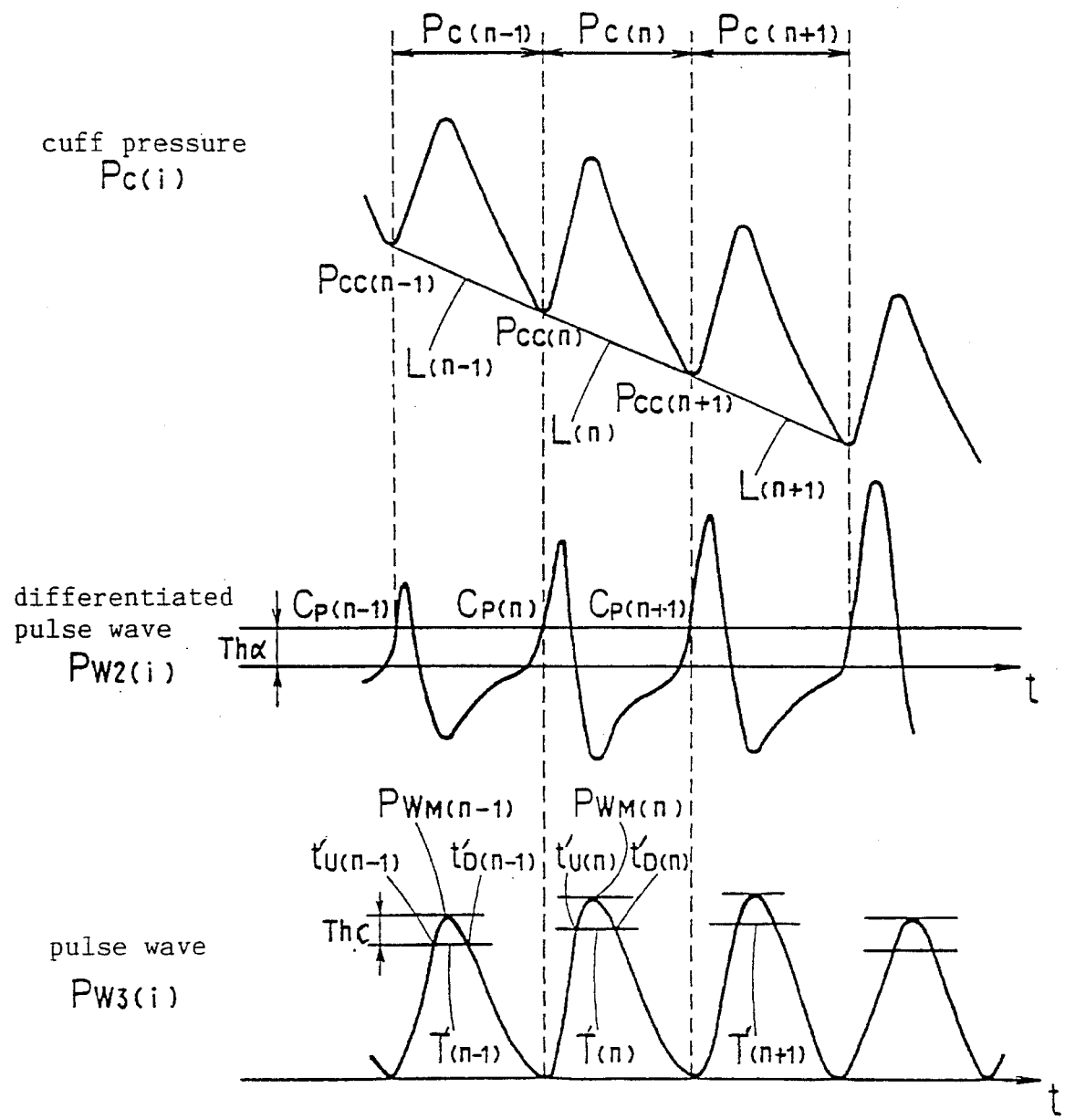
FIG. 4 is a waveform diagram, similar to FIG. 2, for illustrating the process of processing pulse wave data according to a second embodiment of the electronic blood pressure meter of the present invention.
Figure 5:
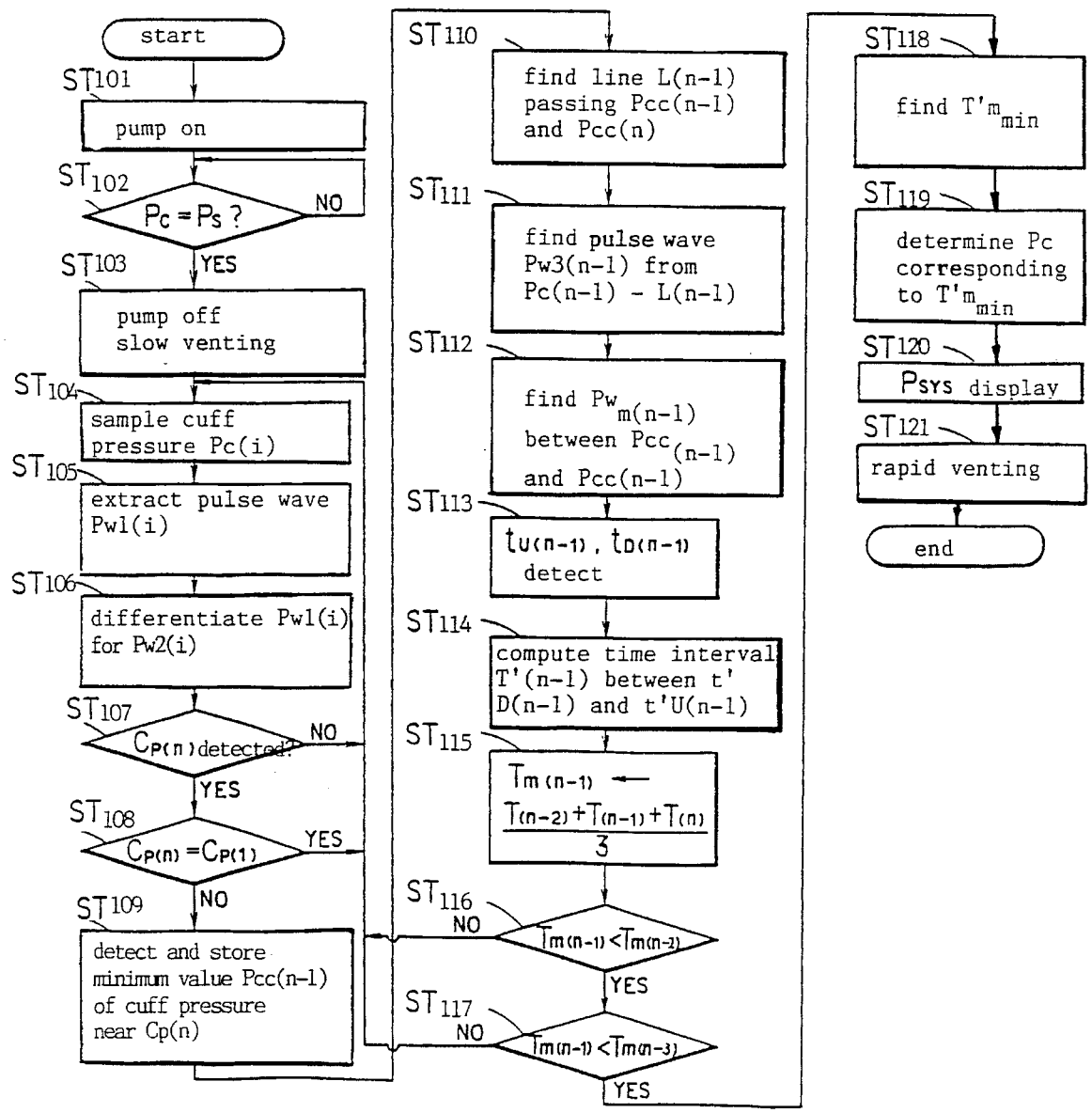
FIG. 5 is a flow diagram, similar to FIG. 3, for illustrating the operation of the second embodiment of the electronic blood pressure meter according to the present invention.

FIG. 4 is a graph showing the working principle of the second embodiment of the present invention, and FIG. 5 is a flow chart of an algorithm, similar to the one shown in FIG. 3, for determining a systolic blood pressure value. In this flow chart, ST101 through ST111 are identical to ST1 through ST11 of the previous embodiment, and description of this part of the flow chart is therefore omitted. As one can readily understand, the following process can be executed with the structure shown in FIG. 1.

In ST112, the maximum value $Pwm_{(n-1)}$ of the pulse wave $Pw_{3(n-1)}$ is detected in the interval between $Pcc_{(n-1)}$ and $Pc_{(n)}$. Further, in ST113 are detected points $t'_{U(n-1)}$ and $t'_{D(n-1)}$ at which $Pw_{3(i)}$ intersects a threshold level Thc as it falls and rises, respectively. The threshold level Thc is typically set between 0.1 and 0.5 mmHg, but may also be a relative value such as so many percent of each peak of the pulse wave $Pw_{3(i)}$ instead of such an absolute value.

In next ST114, a time interval $T'_{(N-1)}$ between $t'_{U(n-1)}$ and $t'_{(N-1)}$ is computed and stored. This time interval $T'_{(N-1)}$ is a variable for evaluating the sharpness of the positive peaks, and the smaller this value is the sharper the peak is.

In ST115, $T'_{(N-1)}$ is smoothed into $T'm_{(N-1)}$ according to equation (3) given below:

$$T'm_{(n-1)}=(T'_{(n-2)}+T'_{(n-1)}+T'_{(n)})/3 \qquad (3)$$

This is performed for the purpose of reducing the effects of such artifact interferences as respiratory irregular pulses and body motions.

In ST116 and ST117, inequalities $T'm_{(n-1)}<T'm_{(n-2)}$ and $T'm_{(n-1)}<T'm_{(N-3)}$ are evaluated; the program flow advances to ST118 only when both the inequalities hold but otherwise returns to ST104.

In ST118, a minimum value is selected from $T'm_{(1)}$ through $T'm_{(N-1)}$ which have been computed so far and is defined as $T'm_{MIN}$. In ST119, the cuff pressure Pc corresponding to $T'm_{MIN}$ is set as a systolic blood pressure value $P_{SYS}$. This systolic blood pressure value $P_{SYS}$ as well as the diastolic blood pressure value $P_{SYS}$ is displayed on the display unit 8 (ST120) and the rapid vent valve 5 is opened to release the upper arm of the subject from pressurization (ST121).

Although the algorithms given in the flow charts of FIGS. 3 and 5 were described as separate embodiments, it is obvious to a person skilled in the art that they can be readily combined into a consolidated process for determining both a systolic blood pressure value and a diastolic blood pressure value, and can be implemented as a single electronic blood pressure meter. Alternatively, it is also possible to determine either a systolic blood pressure value or a diastolic blood pressure value according to one of the above described algorithms and determine the other blood pressure value according to other algorithms which may included conventionally known ones.

Figure 6:
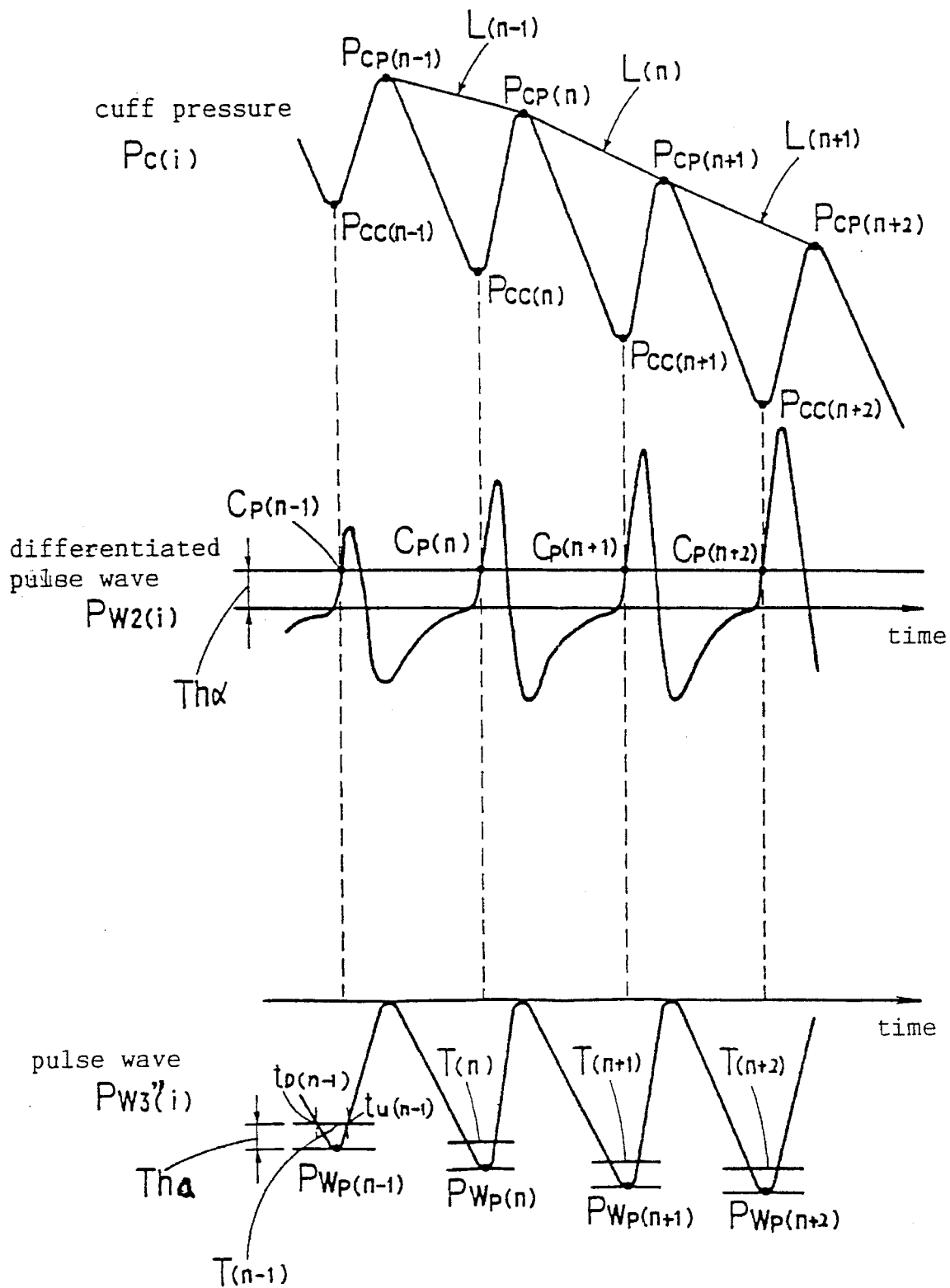
FIG. 6 a waveform diagram illustrating a modified embodiment of the process of processing pulse wave data.
Figure 7:
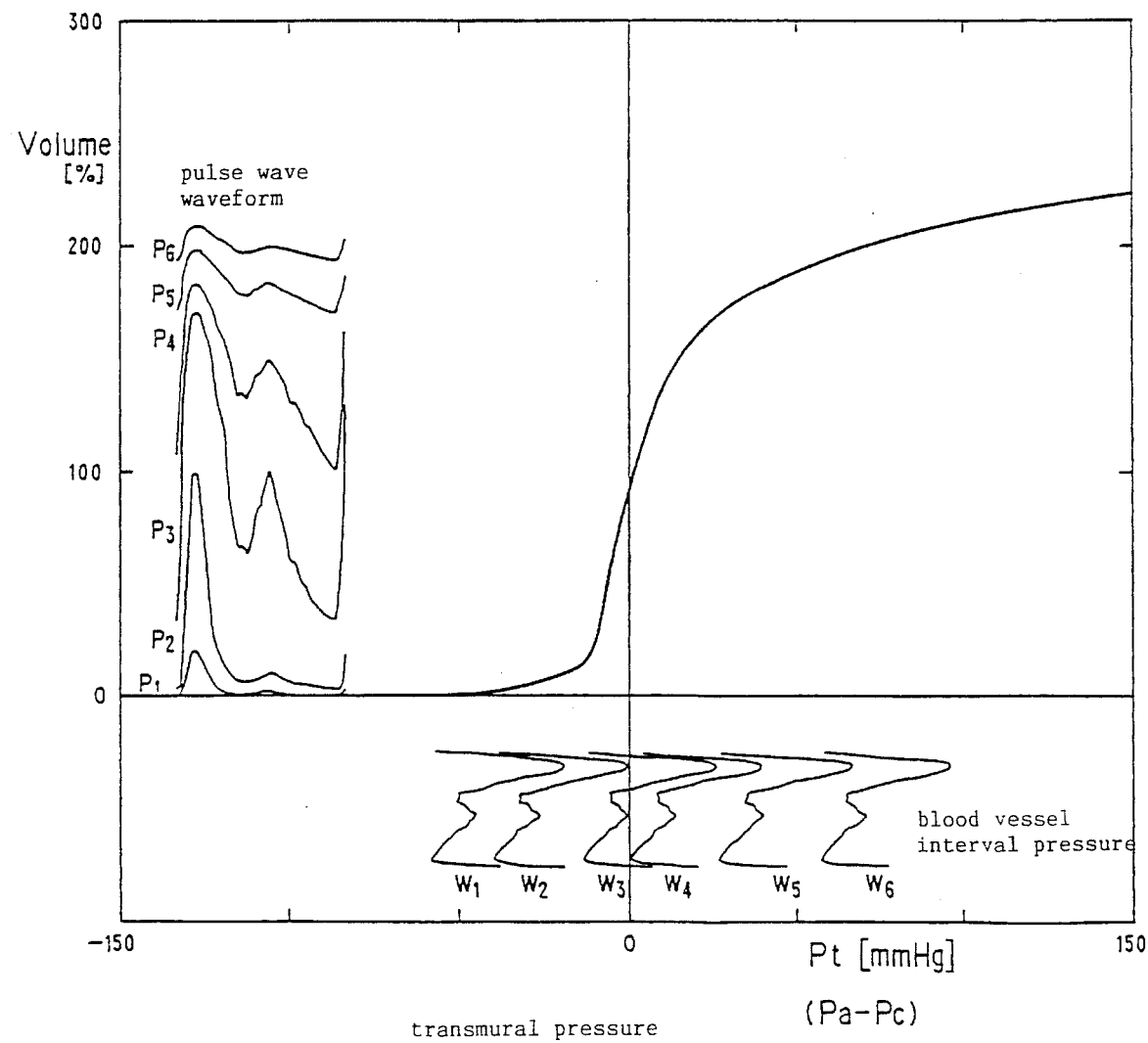
FIG. 7 is a graph showing the relationship between the internal volume of a blood vessel and a transmural pressure for illustrating the working principle of the present invention.
Figure 8A:
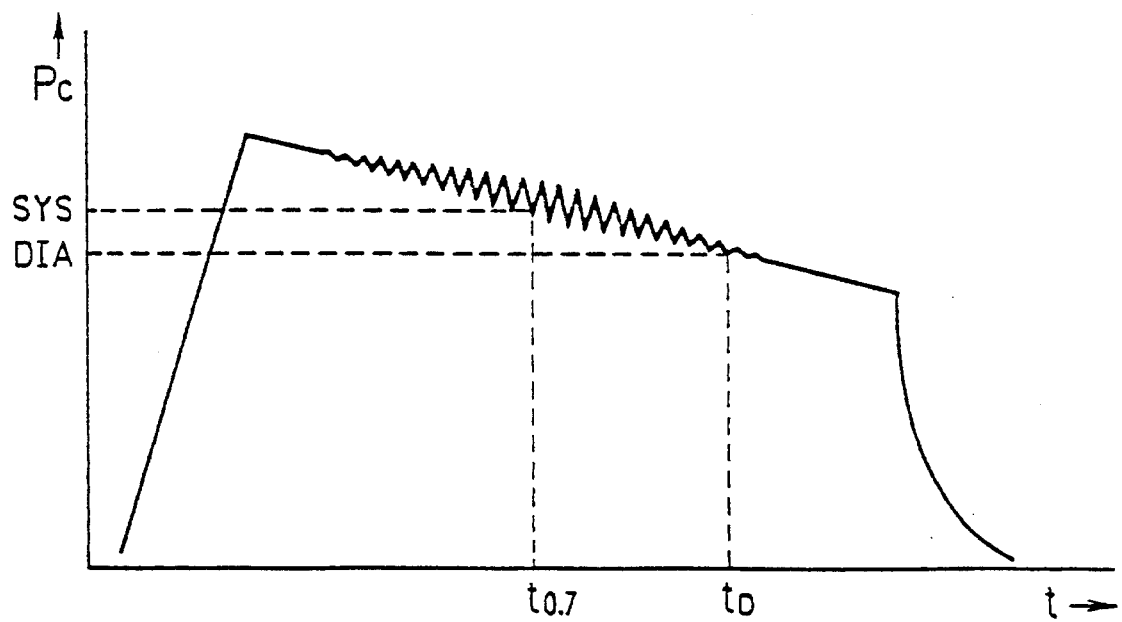
FIGS. 8(a), 8(b) and 8(c) are graphs for showing the principle of determining blood pressure values in a conventional electronic blood pressure meter.
Figure 8B:
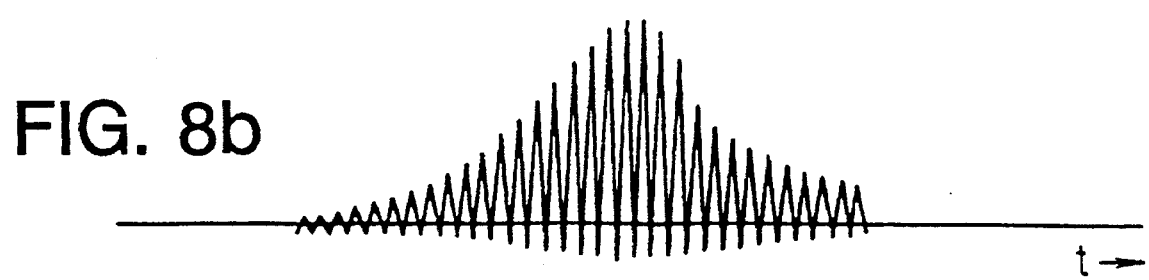
Figure 8C:
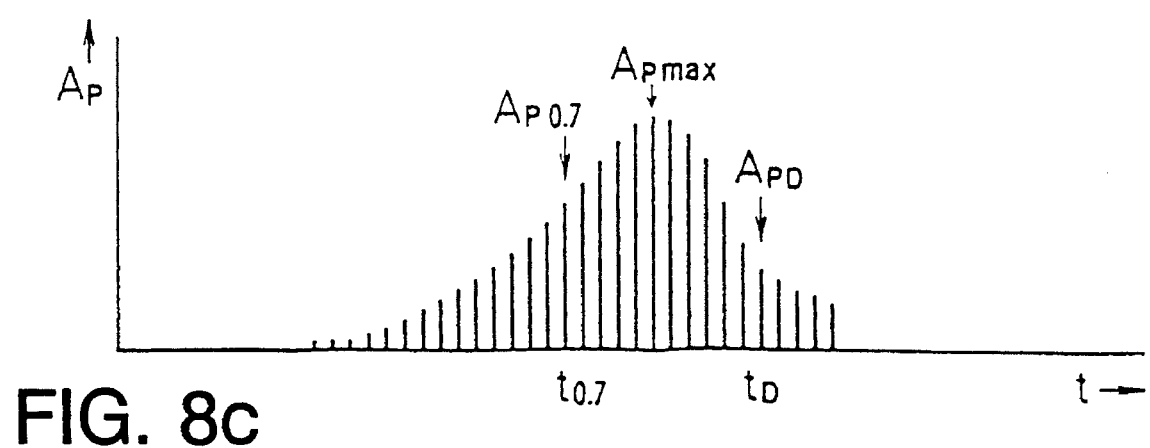

In the above described embodiments, for instance, in the first embodiment, the pulse wave $Pw_{3(i)}$ was obtained by subtracting the line $L_{(n-1)}$ connecting the points of intersection $Pcc_{(N-1)}$ and $Pcc_{(n)}$ from the cuff pressure waveform $Pc_{(n-1)}$, but, alternatively, the process illustrated in FIG. 6 may be used.

According to this process, there is no difference from the above embodiment in that a differentiated pulse wave $Pw_{3''(i)}$ is computed, and $Cp_{(n)}$ is found by applying the condition of exceeding a threshold level Tha for finding the point of intersection $Pcc_{(n)}$ thereof with the cuff pressure waveform $Pc_{(i)}$. Then, the maximum value $Pcp_{(n-1)}$ of the pulse wave $Pc_{(i)}$ in the interval between $Pcc_{(n-1)}$ and $Pcc_{(n)}$ is detected. Then, the line $L_{(n-1)}$ connecting $Pcp_{(n-1)}$ and $Pcp_{(n)}$ is computed. The line $L_{(n-1)}$ is subtracted from the cuff pressure $Pc_{(i)}$ between $Pcp_{(n-1)}$ and $Pcp_{(n)}$ to produce the pulse wave $Pw_{3''(i)}$.

Thereafter, a minimum value $Pwp_{(n)}$ of the pulse wave $Pw_{3''(i)}$ is selected from the interval between $Pcp_{(n-1)}$ and $Pcp_{(n)}$. The point at which a declining part of $Pw_{3(i)}$ intersects the threshold level Thb set above the $Pwp_{(n)}$ is defined as $t_{D(n)}$ and a similar point of intersection of a rising part of $Pw_{3(i)}$ is defined as $t_{U(n)}$. The difference $t_{U(n)}-t_{D(n)}$ is computed and set as $T_{(n)}$. Thereafter, in the same way as in the previous embodiment, a sharpest negative peak is detected according to the comparison of $T_{(n)}$.

The above embodiments pertained to electronic blood pressure meters of an arm band type, but the present invention may also be applied to electronic blood pressure meters for a finger which are based on photoelectrically detected pulse waves.

As described above, the electronic blood pressure meter of the present invention comprises peak extraction means for extracting sharpest peaks of the pulse wave detected by the pulse wave detecting means, and the blood pressure value determining means determines the cuff pressure corresponding to the sharpest negative peak and the sharpest positive peak detected by the peak extraction means as a diastolic blood pressure value and a systolic blood pressure value, respectively. Therefore, the present invention has the advantage of being capable of determining a diastolic blood pressure value and a systolic blood pressure value, both accurately and reliably.

What we claim is:

1. An electronic blood pressure meter, comprising: a cuff; pressurization means for pressurizing fluid in said cuff; depressurization means for rapidly or gradually depressurizing said fluid in said cuff; pressure detecting means for detecting said pressure of said fluid in said cuff; pulse wave detecting means for detecting a pulse wave at a part of a subject to which said cuff is applied; and blood pressure value determining means for determining a blood pressure value according to said fluid pressure detected by said pressure detecting means and said pulse wave detected by said pulse wave detecting means; further comprising:

peak extracting means for extracting a first non-flattened peak from said pulse wave detected by said pulse wave detecting means continuously as said pressure in said cuff decreases, said blood pressure value determining means determining said fluid pressure of said cuff corresponding to said first non-flattened peak detected by said peak extracting means as a blood pressure value wherein said peak extracting means for extracting said first non-flattened peak from said pulse wave comprises:

peak detecting means for detecting peaks of said pulse wave;

intersection detecting means for detecting points of intersection of a level of said pulse wave with a certain threshold level line; and time measurement means for measuring a time interval between each pair of adjacent points of intersection surrounding one of said peaks;

said first non-flattened peak being determined as a peak corresponding to a smallest one of said time intervals.

2. An electronic blood pressure meter according to claim 1, wherein said peaks consist of negative peaks of said pulse wave, and said blood pressure value consists of a diastolic blood pressure value.

3. An electronic blood pressure meter according to claim 1, wherein said peaks consist of positive peaks of said pulse wave, and said blood pressure value consists of a systolic blood pressure value.

4. An electronic blood pressure meter according to claim 1, where said peak extracting means further comprises:

derivative determining means for determining the derivative of said pulse wave;

derivative intersection detecting means for detecting points of intersection of a level of the derivative of said pulse wave determined by said derivative determining means with a certain derivative threshold level line;

where said blood pressure value determining means determines a blood pressure value corresponding to the first non-flattened peak of said pulse wave extracted by said peak extracting means about such derivative intersection points.

5. An electronic blood pressure meter according to claim 4, wherein said peaks consist of negative peaks of said pulse wave, and said blood pressure value consists of a diastolic blood pressure value.

6. An electronic blood pressure meter, comprising: a cuff; pressurization means for pressurizing fluid in said cuff; depressurization means for rapidly or gradually depressurizing said fluid in said cuff; pressure detecting means for detecting said pressure of said fluid in said cuff; pulse wave detecting means for detecting a pulse wave at a part of a subject to which said cuff is applied; and blood pressure value determining means for determining a blood pressure value according to said fluid pressure detected by said pressure detecting means and said pulse wave detected by said pulse wave detecting means; further comprising:

peak extracting means for extracting a first non-flattened peak from said pulse wave detected by said pulse wave detecting means continuously as said pressure in said cuff decreases, said blood pressure value determining means determining said fluid pressure of said cuff corresponding to said first non-flattened peak detected by said peak extracting means as a blood pressure value wherein said peak extracting means for extracting said first non-flattened peak from said pulse wave comprises:

peak detecting means for detecting peaks of said pulse wave;

intersection detecting means for detecting points of intersection of a level of said pulse wave with a certain threshold level line; and time measurement means for measuring the time interval between a point of intersection of said pulse wave level with said threshold level as said pulse wave level is decreasing and a next point of intersection of said pulse wave level with said threshold level as said pulse wave level is increasing;

said blood pressure value consisting of a diastolic blood pressure value, and said first non-flattened peak being determined as a peak corresponding to a smallest one of said time intervals.

7. An electronic blood pressure meter, comprising: a cuff; pressurization means for pressurizing fluid in said cuff; depressurization means for rapidly or gradually depressurizing said fluid in said cuff; pressure detecting means for detecting said pressure of said fluid in said cuff; pulse wave detecting means for detecting a pulse wave at a part of a subject to which said cuff is applied; and blood pressure value determining means for determining a blood pressure value according to said fluid pressure detected by said pressure detecting means and said pulse wave detected by said pulse wave detecting means; further comprising:

peak extracting means for extracting a first non-flattened peak from said pulse wave detected by said pulse wave detecting means continuously as said pressure in said cuff decreases, said blood pressure value determining means determining said fluid pressure of said cuff corresponding to said first non-flattened peak detected by said peak extracting means as a blood pressure value wherein said peak extracting means for extracting said first non-flattened peak from said pulse wave comprises:

peak detecting means for detecting peaks of said pulse wave;

intersection detecting means for detecting points of intersection of a level of said pulse wave with a certain threshold level line; and time measurement means for measuring the time interval between a point of intersection of said pulse wave level with said threshold level as said pulse wave level is increasing and a next point of intersection of said pulse wave level with said threshold level as said pulse wave level is decreasing;

said blood pressure value consisting of a systolic blood pressure value, and said first non-flattened peak being determined as a peak corresponding to a smallest one of said time intervals.

\* \* \* \* \*